United States Patent

Heck

[11] Patent Number: 6,083,207
[45] Date of Patent: Jul. 4, 2000

[54] PARTITIONED HEMOSTASIS VALVE SYSTEM

[75] Inventor: Alicia Heck, Minneapolis, Minn.

[73] Assignee: Daig Corporation, Minnetonka, Minn.

[21] Appl. No.: 09/207,295

[22] Filed: Dec. 8, 1998

[51] Int. Cl.[7] .................................................. A61M 5/00
[52] U.S. Cl. ........................ 604/256; 604/160; 604/164
[58] Field of Search .................................. 604/161, 164, 604/166, 167, 256, 170, 171, 169, 165, 244

[56] References Cited

U.S. PATENT DOCUMENTS

| | | |
|---|---|---|
| Re. 31,855 | 3/1985 | Osborne . |
| 4,166,469 | 9/1979 | Littleford . |
| 4,243,050 | 1/1981 | Littleford . |
| 4,345,606 | 8/1982 | Littleford . |
| 4,451,256 | 5/1984 | Weikl et al. . |
| 4,581,025 | 4/1986 | Timmermans . |
| 4,596,559 | 6/1986 | Fleischhacker . |
| 4,909,798 | 3/1990 | Fleischhacker . |
| 4,983,168 | 1/1991 | Moorehead . |
| 5,092,857 | 3/1992 | Fleischhacker . |
| 5,098,392 | 3/1992 | Fleischhacker . |
| 5,125,904 | 6/1992 | Lee . |
| 5,192,857 | 3/1993 | Etwiler . |
| 5,312,355 | 5/1994 | Lee . |
| 5,397,311 | 3/1995 | Walker et al. . |
| 5,429,619 | 7/1995 | Furnish . |
| 5,441,504 | 8/1995 | Pohndorf et al. . |
| 5,613,953 | 3/1997 | Pohndorf . |
| 5,755,693 | 5/1998 | Walker et al. . |

*Primary Examiner*—Wynn Wood Coggins
*Assistant Examiner*—Deborah Blyveis
*Attorney, Agent, or Firm*—Scott R. Cox

[57] ABSTRACT

A partitioned hemostasis valve system for use with a splittable sheath, including a partitioned hemostasis valve housing which holds a partitioned hemostasis valve formed in at least two separate and distinct sections. Pivotable wing portions are secured to the partitioned valve housing such that upon pressure being placed on these wing portions, the separate sides of the partitioned hemostasis valve housing and the partitioned hemostasis valve are separated. The partitioned hemostasis valve system may also include a splittable adaptor system for securing to a splittable sheath.

29 Claims, 8 Drawing Sheets

PARTITIONED HEMOSTASIS VALVE SYSTEM

FIELD OF INVENTION

This invention relates to the field of hemostasis valves. More particularly the invention relates to a partitioned hemostasis valve system which includes a partitioned hemostasis valve contained within a partitioned hemostasis valve housing for attachment to a splittable sheath for use during introduction of a medical device, preferably a pacemaker lead, into a human body.

BACKGROUND

There are a number of medical procedures which require the introduction of medical instruments into arteries and veins. In one such procedure, known as the Seldinger procedure, a surgical opening is made in a vein or artery with a needle. A guide wire is then inserted through the lumen of the needle into the vein or artery. The needle is withdrawn, leaving the guide wire in place. A dilator is then inserted over the guide wire inside an associated sheath. The dilator and guidewire are removed once the sheath is in place. At this point, various types of catheters or leads may be inserted into the vessel within the lumen of the sheath using the sheath as a conduit to prevent damage to the vessel wall.

In conventional procedures, these sheaths often include hemostasis valves. In many cases the hemostasis valve is designed for use with a specific size of a catheter. Such hemostasis valves have been disclosed, for example, in U.S. Pat. Nos. 5,092,857 and 4,909,798.

In medical procedures where a pacemaker lead is inserted into a patient, a sheath is normally used to guide the pacemaker lead to the appropriate location. Before the pacemaker lead is permanently secured in place and attached to a pacemaker, the sheath must be removed. Because of the size of its lumen, the sheath cannot simply slip over the exterior end of the pacemaker lead as that end of the lead contains a connector coupling for connection to the pacemaker.

Accordingly, there have been disclosed a number of sheaths for use in the introduction of pacemaker leads, which can be split in half while still surrounding the pacemaker lead. In this use, once the pacemaker lead is in place, the sheath is longitudinally severed and removed from the pacemaker lead. For example, U.S. Pat. No. 4,983,168 discloses such a layered, peel-away hollow sheath, wherein the sheath wall is comprised of at least two layers, an inside cylindrical layer and an outside layer comprising two semi-cylindrical segments defining opposed axially-directed slits or slots therebetween, which comprise tear lines. U.S. Pat. No. 4,596,559 discloses a tear away sheath for use with a disposable introducer set in conjunction with a catheter. U.S. Pat. No. Re. 31,855 discloses a sheath that has an internal molecular orientation which tears easily in a lengthwise direction and with great difficulty in a crosswise or oblique direction. See also U.S. Pat. No. 4,581,025. Longitudinally scored or perforated sheaths are disclosed in U.S. Pat. Nos. 4,166,469; 4,243,050; 4,345,606 and 4,451,256. A locking dilator for use with peel-away sheaths is disclosed in U.S. Pat. No. 5,098,392.

A problem has developed during the use of these splittable sheaths. During the introduction of a pacemaker lead, a significant amount of bleeding may occur at the operation site, depending upon the blood pressure present in the vessel. Once the sheath is in place within a vessel, it provides a passageway for the free flow of blood away from the operation site.

Further, because of this flow of blood, clotting may occur if the sheath remains in position for an extended period of time. These clots may cause emboli which may pass to the lung and have a detrimental impact on the patent.

These sheaths may also provide a passageway for the introduction of air into the vessel. The inadvertent introduction of air into the blood system can cause air emboli in the patient which may have negative effects.

Because of these problems these splittable sheaths are removed from the theater of operation as soon as possible, even if it would be preferable to maintain them in position for a longer period of time. Such hurried procedures can result in errors or medical complications.

One method of preventing, or at least limiting, the flow of blood out of a sheath while a pacemaker lead is being introduced is for the physician to place his thumb over the exposed end of the sheath or to squeeze or pinch the exposed end of the sheath between his thumb and forefinger. However, neither of these methods for reducing the undesired flow of blood and air through the sheath is desirable, because the opportunity for loss of blood and introduction of air is still present. In addition, the structure of these sheaths still requires the surgeon to hold onto it while it is in place in the vessel, thereby limiting the surgeon's ability to perform other medical procedures at the same time. Moreover, squeezing the exposed end of the sheath can deform or even break the sheath, making lead insertion difficult and increasing the likelihood of damage to the lead as it passes through the sheath. Further, even when holding the end of the sheath or pinching the sheath, flow of blood out of the sheath is not entirely stopped.

Thus, the introduction of a hemostasis valve into a sheath to limit blood flow would be helpful during the introduction of pacemaker leads into the heart and other similar medical procedures. However, because the exterior end of pacemaker leads is larger than the opening in conventional hemostasis valves, it is not possible for pacemaker leads to pass through these conventional hemostasis valves. Accordingly, splittable hemostasis valves contained within splittable sheaths for the introduction of pacemaker leads have been disclosed, for example, in U.S. Pat. Nos. 5,312,355 and 5,125,904. Each of these patents discloses a splittable sheath valve body (16), a splittable sheath valve assembly (14) and a splittable valve membrane (22). To remove the splittable sheath valve assembly (14) from around the pacemaker lead after the lead has been placed within the heart, the splittable sheath valve body (16) and the splittable sheath valve assembly (14) are torn apart along score lines (34, 36) by placing pressure on the flanges (38, 40) of the splittable sheath valve body (16). The splittable valve membrane (22) is also torn apart during this procedure along a weakened line or score line in the splittable valve membrane (22), or, as shown in U.S. Pat. No. 5,312,355, along a Y-shaped cut in the splittable valve membrane (22).

Another valve system incorporated into a splittable sheath for the introduction of pacemaker leads is disclosed in U.S. Pat. No. 5,441,504. A slidable valve (70) secured on a tab (62) of the sheath (40) can be slid to cover the opening in the sheath (40) during introduction of the pacemaker lead. When it is necessary to remove the sheath (40) from the operating theater, the sheath (40) is split along score line (86) with each side of the slidable valve (70) remaining secured to one tab (62) of the splittable sheath (40).

Another splittable sheath containing a splittable valve is disclosed in U.S. Pat. Nos. 5,397,311 and 5,755,693. These patents disclose a valve (30, 30A, 30B or 30C) or a valve system comprising a pair of valves (78, 80) contained within the body of a splittable sheath (18) to prevent the flow of blood through the splittable sheath (18). The valve may comprise a pair of semicircular members, each of which may include a slit, as shown, for example, in FIGS. 7 and 8 of those patents.

An additional splittable sheath system containing a valve that splits is disclosed in U.S. Pat. No. 5,613,953. The valve members (82 and 82A) are part of the handles of the splittable sheath and are separated into separate valve halves by the separation of the exposed handles (90 and 90A) of the splittable sheath. The handles and the valve members are cooperatively connected by a rotatable link assembly (100, 100A), which is biased into a closed position by integrally formed bias springs.

The devices that have been previously disclosed often have difficulty in being split when used in a medical procedure because of the presence of fluids, particularly blood. In addition, when these prior art devices are split, blood splattering often occurs when the hemostasis valve is torn. Further, the valve often tears unevenly, making it more difficult to remove the splittable sheath and splittable valve. Some physicians are also hesitant to force the tines of leads for pacemakers through these valves because they fear damage to the tines.

In addition, some physicians may want to delay the introduction of a hemostasis valve into the sheath even after the sheath is already in position.

Further, it is sometimes necessary to remove the hemostasis valve from the operating theater at a time when the sheath is still in use.

Thus, it is important to have a device to hold the hemostasis valve which is separate and distinct from the splittable sheath itself.

It is also important to provide an improved partitioned device for holding a partitioned hemostasis valve which can be secured to a splittable sheath and utilized for the introduction of a pacemaker lead into the heart.

Therefore, it is an object of this invention to provide an improved partitioned hemostasis valve system.

It is a further object of the invention to provide a partitioned hemostasis valve system that can be secured to a separate and distinct splittable sheath for the introduction of medical devices into the heart, particularly pacemaker leads.

It is a further object of this invention to disclose a partitioned hemostasis valve system containing an adaptor system for securing the hemostasis valve system to a splittable sheath.

It is a still further object of the invention to disclose a partitioned hemostasis valve system which includes a partitioned hemostasis valve held within a partitioned hemostasis valve housing and a splittable sheath.

It is a still further object of the invention to disclose a partitioned hemostasis valve system which can be secured to a splittable sheath and removed from the splittable sheath without tearing the hemostasis valve.

It is a still further object of the invention to disclose a partitioned hemostasis valve system which includes a partitioned hemostasis valve housing containing a partitioned hemostasis valve and a hemostasis valve separation system.

It is a still further object of the invention to disclose a partitioned hemostasis valve system which includes a partitioned hemostasis valve for use with a splittable sheath which can be removed from a position of surrounding an electrode lead without tearing the splittable sheath.

It is a still further object of the invention to disclose a partitioned hemostasis valve system enclosed within a partitioned hemostasis valve housing, which housing can be locked in a closed position and unlocked in an open position.

It is a further object of the invention to disclose a partitioned hemostasis valve housing containing pivotable wing portions which force the separate sides of a partitioned hemostasis valve together.

It is a still further object of the invention to disclose a partitioned hemostasis valve system which includes a partitioned hemostasis valve formed from a pair of hemostasis valve sections joined together by an extended seal.

These and other objects and features of the present invention will become apparent to those skilled in the art from a consideration of the following detailed description and claims. The description, along with any drawings, provides a selected example of the construction of the device to illustrate the invention.

SUMMARY OF INVENTION

In accordance with the present invention there is provided a partitioned hemostasis valve system which includes a partitioned hemostasis valve housing containing a central chamber, a partitioned hemostasis valve secured within the chamber, a hemostasis valve separation system, secured to the partitioned hemostasis valve housing and designed to separate the partitioned sections of both the housing and the hemostasis valve, and a partitioned adaptor system which permits the partitioned hemostasis valve system to be attached to a splittable sheath.

Preferably the hemostasis valve separation system includes pivotable wing portions, pivot pin openings, a pivot pin and a spring which urges the separate sections of the partitioned hemostasis valve together.

Also disclosed is a process of the use of the partitioned hemostasis valve system, including introducing a splittable sheath into a vessel, securing a partitioned hemostasis valve system to the splittable sheath, wherein the partitioned hemostasis valve system includes a partitioned hemostasis valve housing containing a central chamber, a partitioned hemostasis valve secured within the central chamber of the partitioned hemostasis valve housing, and a hemostasis valve separation system, secured to the partitioned hemostasis valve housing and structured to permit separation of the partitioned portions of the housing and the hemostasis valve.

DETAILED DESCRIPTION OF THE INVENTION

Figure 1:
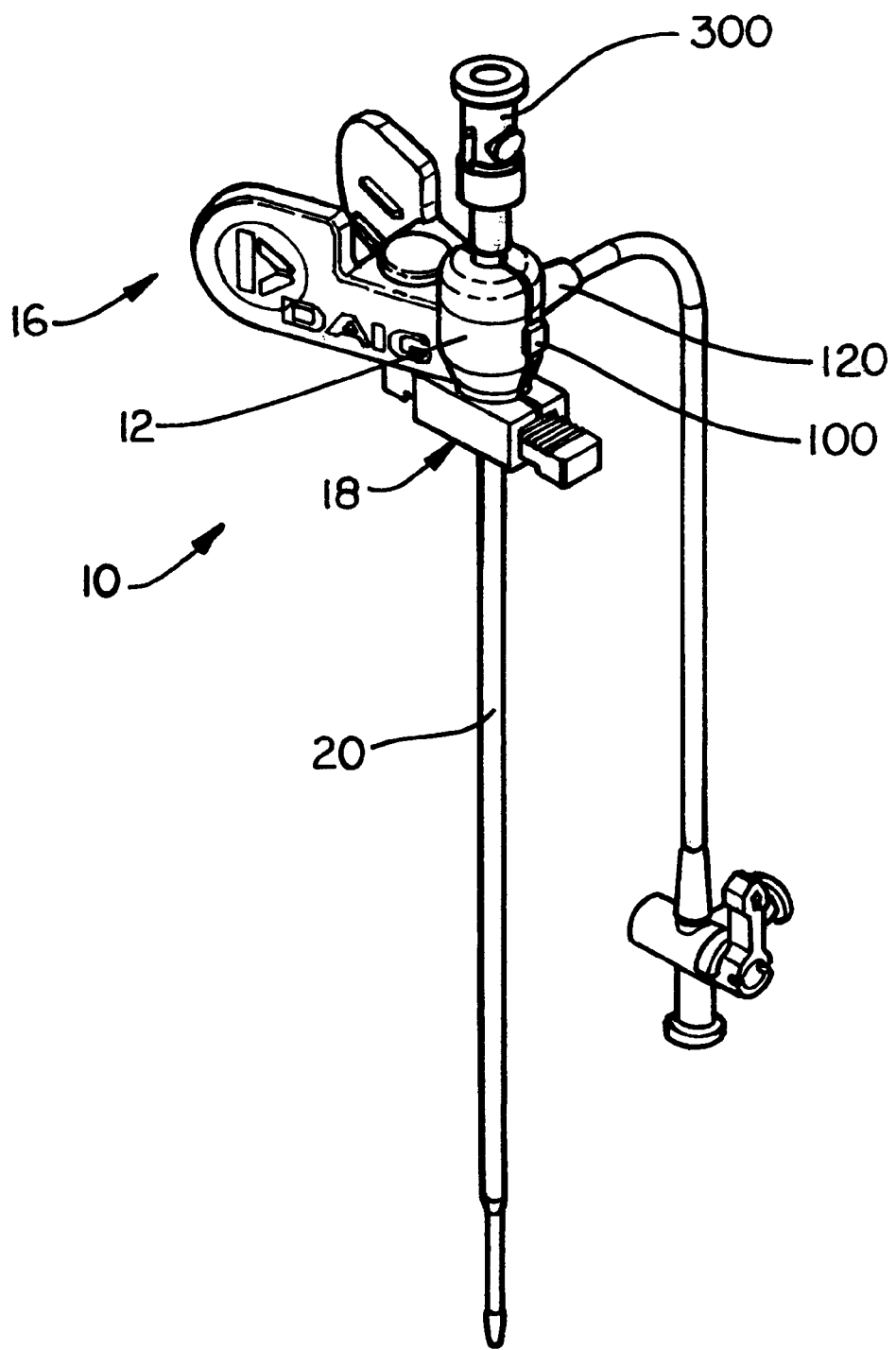
FIG. 1 is a perspective view of the partitioned hemostasis valve system with a dilator inserted therein and a side port extension with stopcock secured thereto, wherein the partitioned hemostasis valve system is secured to a splittable sheath.
Figure 2:
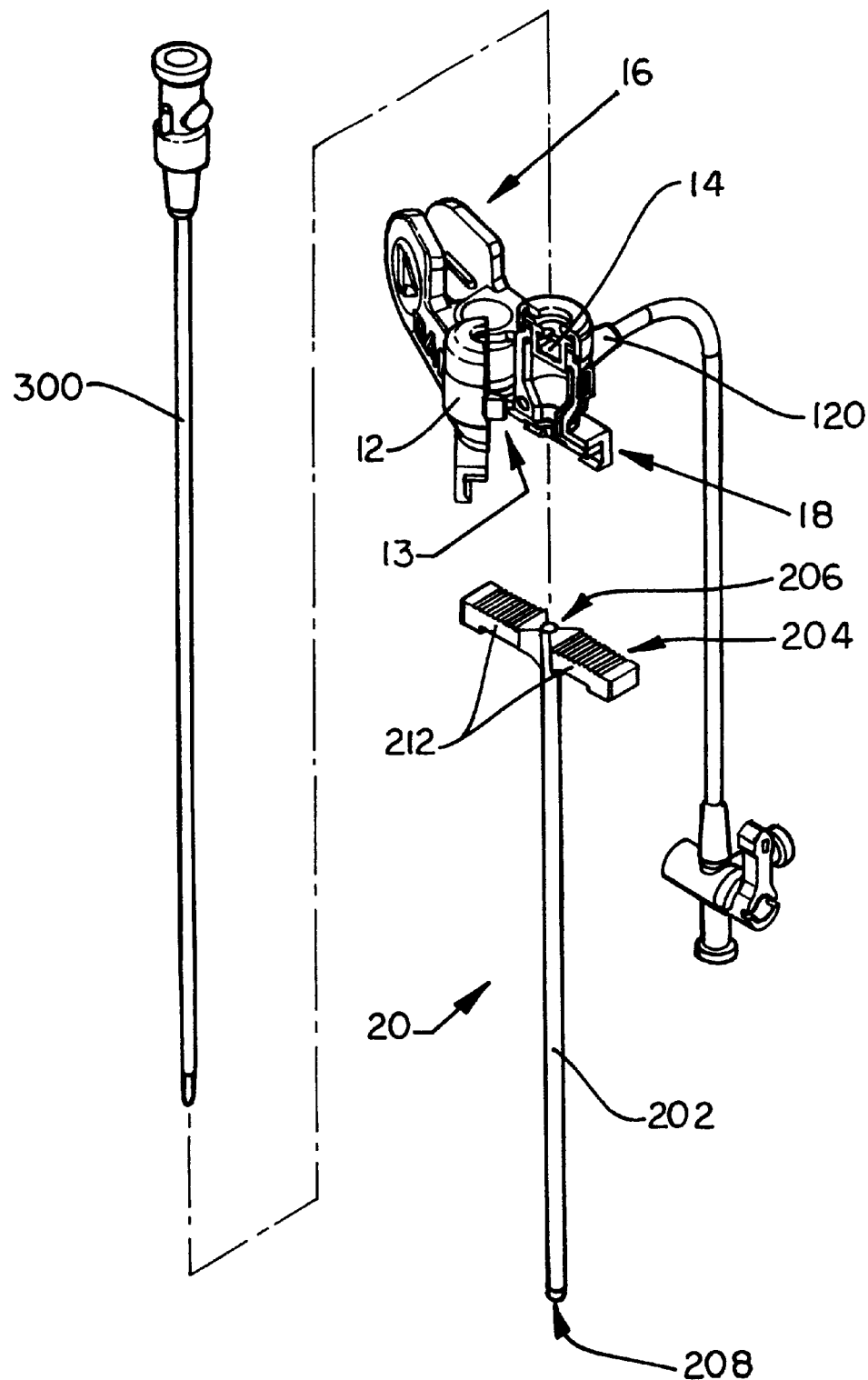
FIG. 2 is an exploded view of the partitioned hemostasis valve system of FIG. 1 with dilator, side port extension with stopcock and splittable sheath.

The partitioned hemostasis valve system (10) of the present invention, as shown in FIGS. 1 and 2, includes a partitioned hemostasis valve housing (12), a partitioned hemostasis valve (14) secured within a central chamber (13) within that housing (12), a hemostasis valve separation system (16) forming an element of the partitioned hemostasis valve housing (12), and an adaptor system (18), secured to the partitioned hemostasis valve housing (12), by which a splittable sheath (20) can be secured to the partitioned hemostasis valve system (10).

Figure 3:
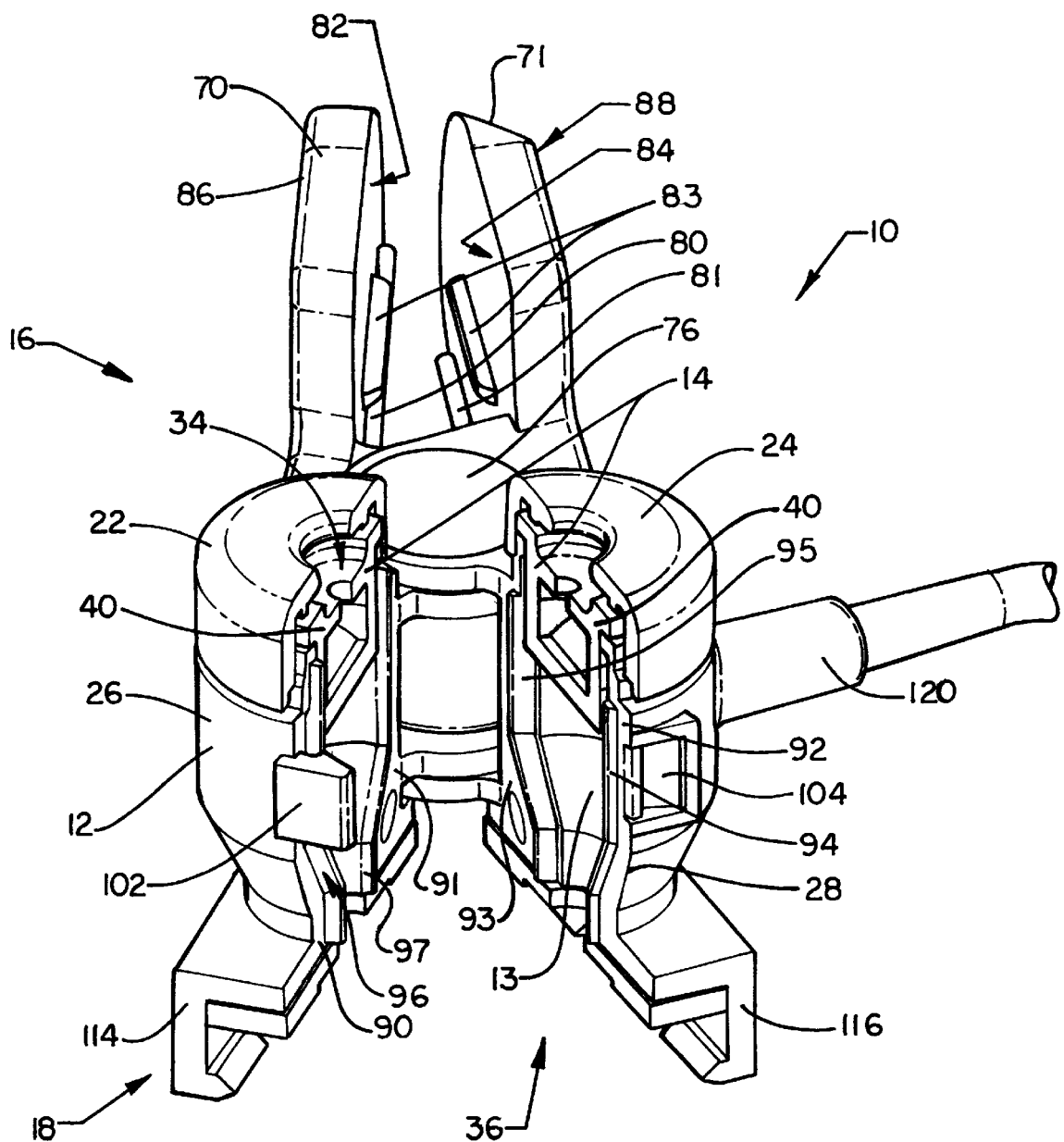
FIG. 3 is a perspective view of the partitioned hemostasis valve system with body sections of the partitioned hemostasis valve housing placed in an open position.
Figure 4:
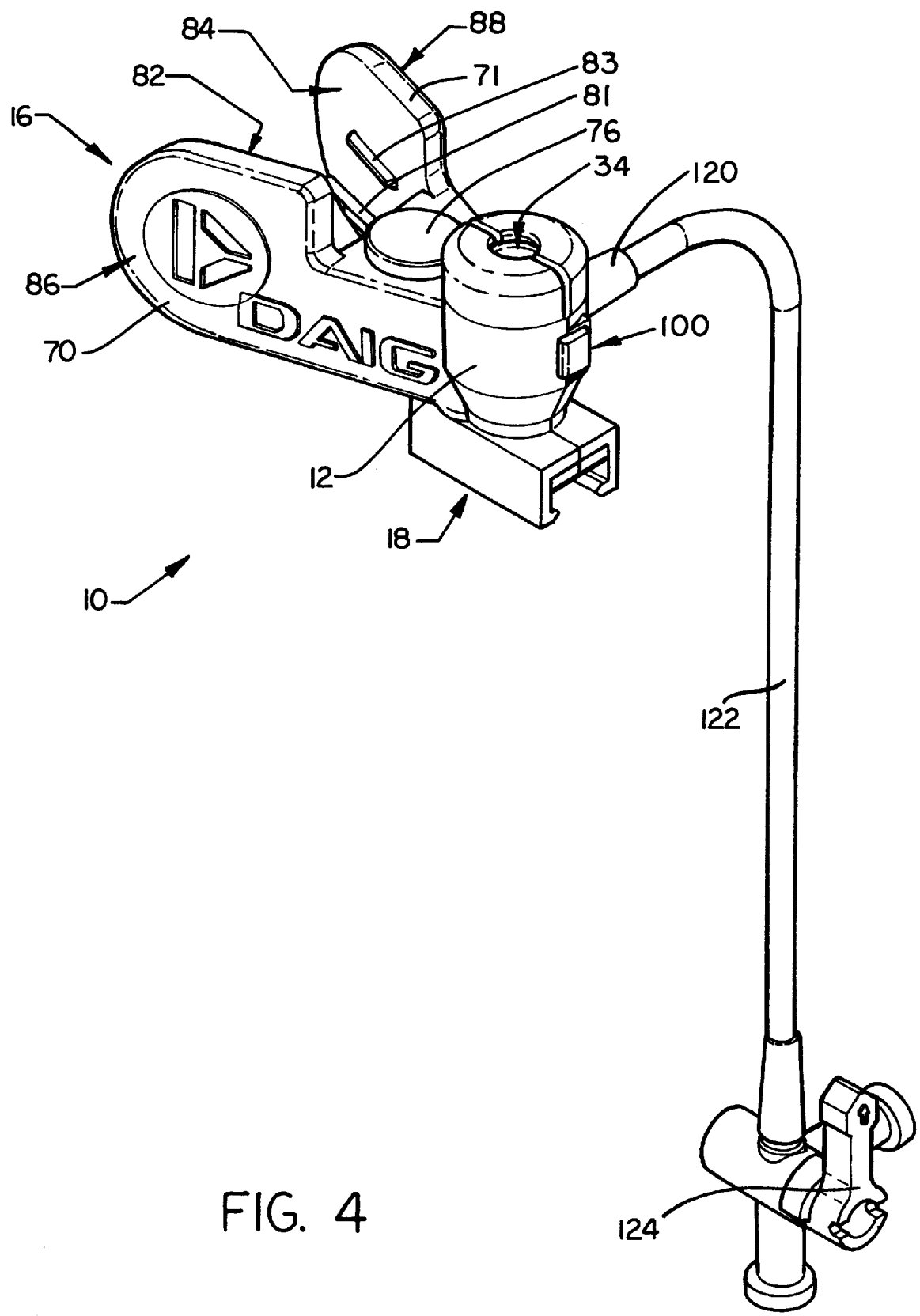
FIG. 4 is a perspective view of the partitioned hemostasis valve system secured to a side port extension with stopcock with the body sections of the partitioned hemostasis valve housing placed in a closed position.
Figure 5:
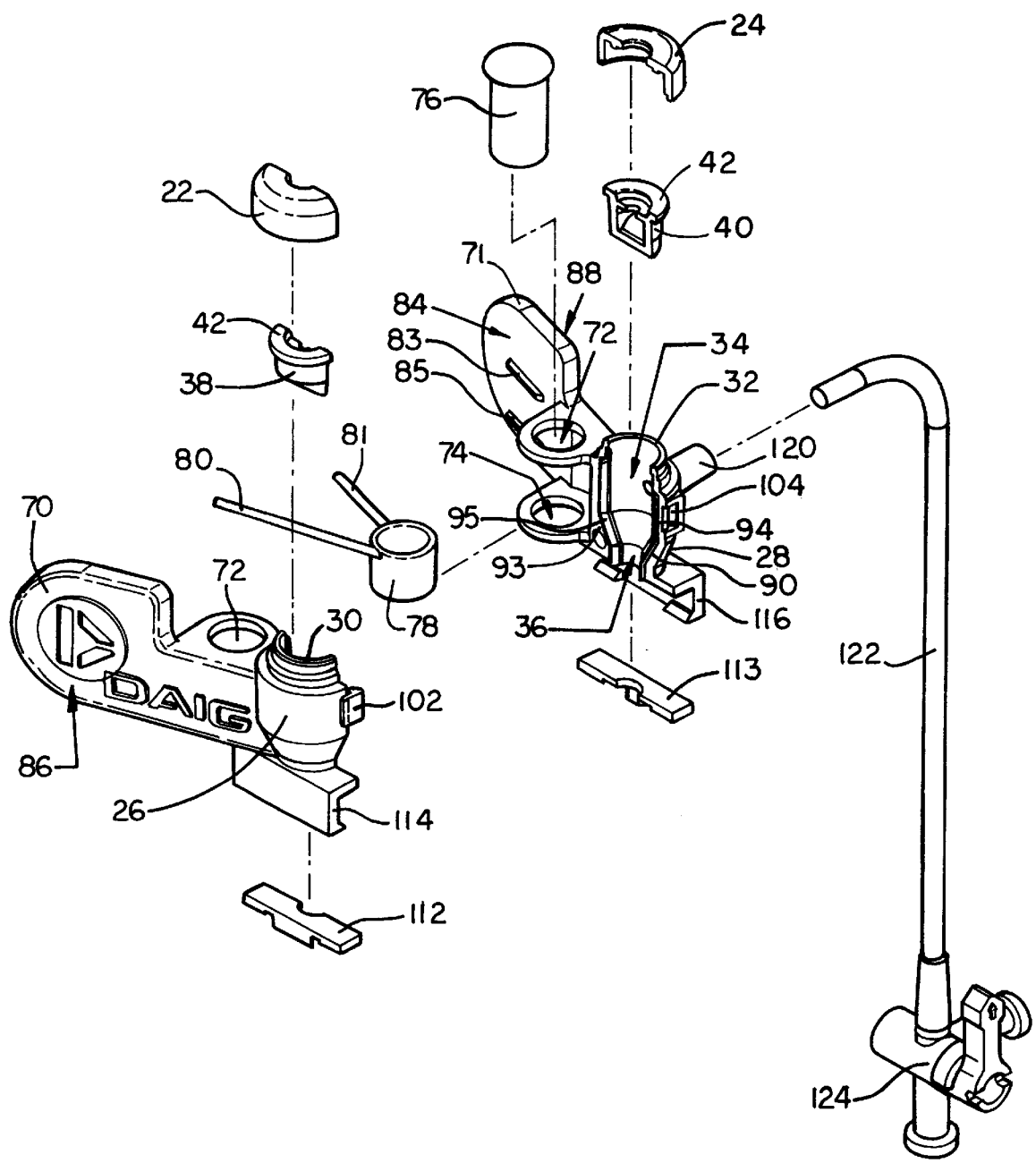
FIG. 5 is an exploded view of the partitioned hemostasis valve system with a side port extension with stopcock.

The partitioned hemostasis valve housing (12), as shown in FIG. 3, includes a first (34) and second (36) opposing open ends to permit insertion of a dilator (300), catheter or pacemaker lead or other medical device into and through the central chamber (13) of the partitioned hemostasis valve housing (12). As shown in FIGS. 3, 4, and 5, the partitioned hemostasis valve housing (12) also includes a pair of cap sections (22, 24) secured onto a pair of hemostasis valve body sections (26, 28). The cap sections (22, 24) and the body sections (26, 28) of the partitioned hemostasis valve housing (12) are formed from a relatively hard plastic, such as ABS resins or a high density polyethylene. Each of the cap sections (22, 24) is secured to a separate body section (26, 28) by a conventional securing method, such as ultrasonic bonding, heat sealing, or gluing.

Secured within the central chamber (13) of the body sections (26, 28) of the partitioned hemostasis valve housing (12) as shown in FIG. 3 is the partitioned hemostasis valve (14). The partitioned hemostasis valve (14) is preferably formed from two hemostasis valve sections (38, 40). Each section (38,40) of the partitioned hemostasis valve (14) is secured within one of the body sections (26, 28) of the partitioned hemostasis valve housing (12). Each section (38, 40) of the partitioned hemostasis valve (14) is formed from a conventional hemostasis valve material, such as a pliant, resilient rubber, such as silicon rubber, latex rubber or a foamed rubber of 20 to 60 durometer, which can be shaped to fit within the respective body sections (26, 28) of the partitioned hemostasis valve housing (12).

In a preferred embodiment, the partitioned hemostasis valve (14) consists of two equal-sized valve sections (38, 40), one secured into each of the body sections (26, 28) of the partitioned hemostasis valve housing (12). Alternatively, the valve sections (38, 40) of the partitioned hemostasis valve (14) and the body sections (26, 28) of the partitioned hemostasis valve housing (12) can be produced from multiple sections with the same or a different size.

Each hemostasis valve section (38, 40) is placed within one of the body sections (26, 28) of the partitioned hemostasis valve housing (12), and is secured in place, preferably by the respective cap sections (22, 24). Each of the cap sections (22, 24) sandwiches a top portion (42) of the respective hemostasis valve sections (38, 40) against a top lip (30, 32) of the respective body section (26, 28) of the partitioned hemostasis valve housing (12), as shown in FIGS. 3 and 5.

In a preferred embodiment, each hemostasis valve section (38) is the mirror image of the opposite hemostasis valve section (40). The overall shape of the pair of hemostasis valve sections (38,40) of the partitioned hemostasis valve (14) when combined may be the same overall shape as that of a conventional hemostasis valve, such as is disclosed in U.S. Pat. Nos. 5,192,857, 5,092,857 and 4,909,798, or it may be different. Notwithstanding, it is important that the partitioned hemostasis valve (14) when secured within the partitioned hemostasis valve housing (14) be maintained in separate, but distinct hemostasis valve sections (38, 40) which are not physically secured to each other, but rather are forced together by the action of the partitioned hemostasis valve housing (12).

Figure 6:
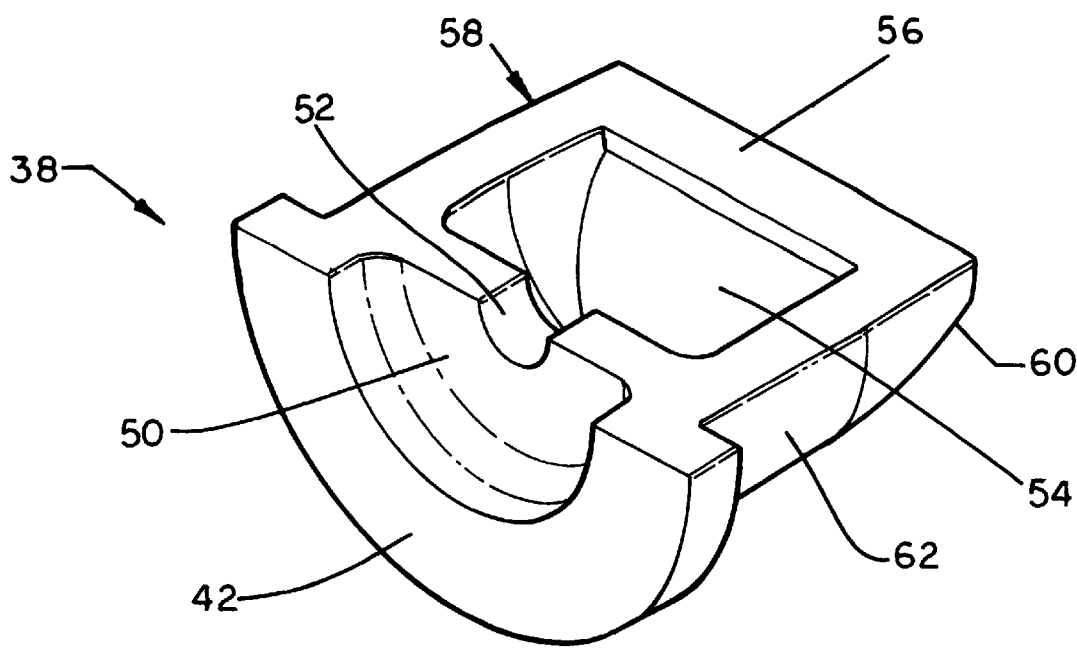
FIG. 6 is a perspective view of one of the partitioned hemostasis valve sections of the partitioned hemostasis valve.
Figure 7:
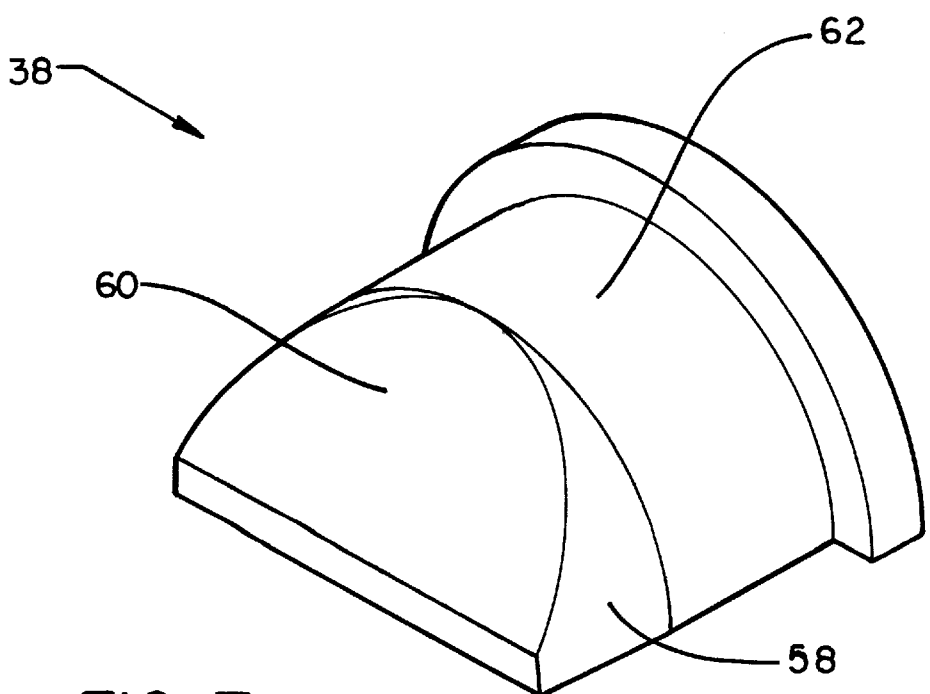
FIG. 7 is a perspective view of the hemostasis valve section of FIG. 6 rotated 180 degrees.
Figure 8:
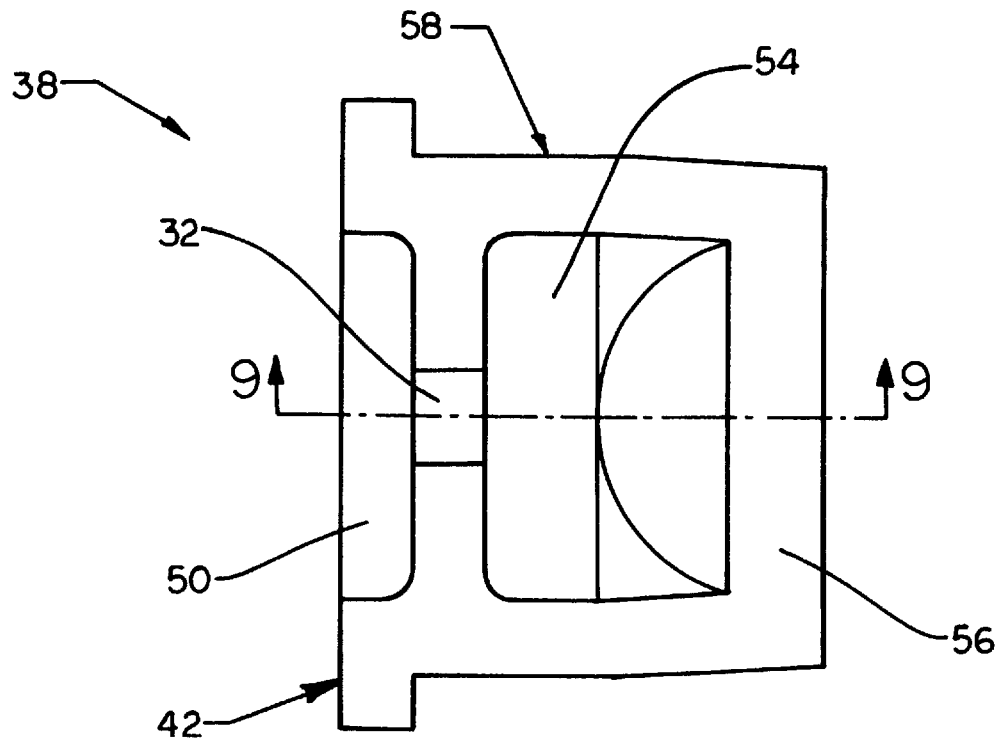
FIG. 8 is a top view of the partitioned hemostasis valve section of FIG. 6.
Figure 9:
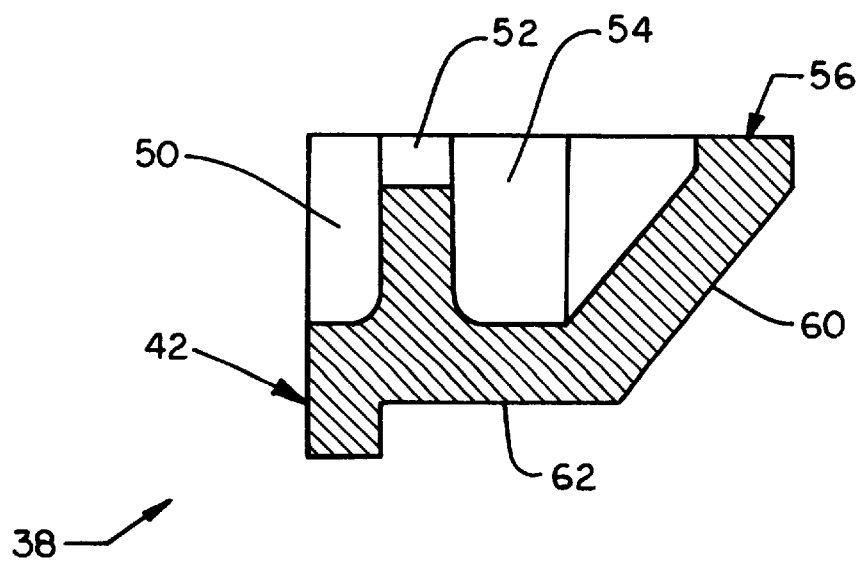
FIG. 9 is a side view of the partitioned hemostasis valve section of FIG. 8 taken along line 9—9.

The hemostasis valve sections (38, 40) of the partitioned hemostasis valve (14) preferably are formed in a unique shape, as shown in FIGS. 6, 7, 8 and 9. Each hemostasis valve section (38, 40) includes a top (42), which is sandwiched between the respective cap section (22) and the top (30) of the respective body section (26), and a receiving area (50) into which a medical device can be inserted. The receiving area (50) extends downward into a neck opening (52) through which the medical device passes. The neck opening (52) communicates between the receiving area (50) and a sealing chamber (54). The sealing chamber (54) communicates between the neck opening (52) and a lip (56) of the hemostasis valve section (38), as best shown in FIGS. 6, 8 and 9.

The outside wall (58) of the hemostasis valve section (38) as shown in FIGS. 7 and 9 includes a lower, inwardly sloped portion (60) which slopes inwardly as it approaches the lip (56), and an upper portion (62). This inwardly sloped portion (60) of the outside wall (58) provides support for the lip (56) when it joins with the corresponding lip (56) of the other cooperating hemostasis valve section (40). In addition, by sloping inward toward the lip (56), the inwardly sloped portion (60) of the outside wall (58) provides space for the lips (56) to separate without excessive force being applied, as the medical device passes through the lips (56). The inwardly sloped portion (60) of the outside wall (58) preferably slopes at an angle of about 35 to about 75 degrees from the position of the upper portion (62) so that it places pressure on the lip (56) to hold it closed against the corresponding lip of the cooperating hemostasis valve section (40), even when the medical device is forced between the lips (56). In addition, the upper portion (62) preferably extends downward from the top (42), preferably perpendicular to that top (42), and provides additional support for the inwardly sloped portion (60) of the outside wall (58) by making contact with the inner wall surface of the sealing chamber (54). An additional sloping section (not shown), sloping inwardly toward the lips (56), may also be provided in the outside wall (58) near the lips (56) to prevent the lips from opening when no pressure is placed on them by the medical device.

When the body sections (26, 28) of the partitioned hemostasis valve housing (12) are joined together, they force the separate hemostasis valve sections (38, 40) against each other forming the complete, partitioned hemostasis valve (14).

In a preferred embodiment, the partitioned hemostasis valve housing (12) when secured to the hemostasis valve separating system (16) takes the general shape of a clothes pin, as shown in FIGS. 3, 4 and 5. The partitioned hemostasis valve separation system (16) includes wing sections (70, 71), a pair of pivot pin openings (72, 74) present in each wing section (70, 71), a pivot pin (76) and a spring (78), as shown in FIG. 5. The pivot pin (76) is inserted in the pair of pivot pin openings (72, 74) which are provided in each of the wing sections (70, 71).

The spring (78) is placed over the pivot pin (76) and is held in place between the pair of openings (72, 74) in each wing section (70, 71). The spring (78) preferably has a pair of extension arms (80, 81), each of which extend outward from the spring (78) and rest against the inside surfaces (82, 84) of each wing section (70 and 71) between a pair of support ribs (83,85) secured to the inside surfaces (82, 84) of each wing section (70, 71). Because the spring (78) is maintained on the pivot pin (76) under tension, these arms (80, 81) force the wing sections (70 and 71) apart and correspondingly force the inner edges (90, 91, 92 and 93) of the body sections (26, 28) of the partitioned hemostasis valve housing (12) together, thus closing the partitioned hemostasis valve housing (12), as shown in FIGS. 1 and 4. In this arrangement the respective body sections (26, 28) of the partitioned hemostasis valve housing (12) also forces the respective hemostasis valve sections (38, 40) of the partitioned hemostasis valve (14) together to form the complete partitioned hemostasis valve (14).

Inward pressure on the wing sections (70, 71) forces the respective hemostasis valve sections (38, 40) of the partitioned hemostasis valve (14) apart to separate the respective hemostasis valve sections (38, 40). When sufficient inward pressure is placed on the outside surfaces (86, 88) of the respective wing sections (70, 71), the respective body sections (26, 28) pivot around the pivot pin (76) to an open position, as shown in FIGS. 2 and 3. Any structure which permits the respective body sections (26, 28) of the partitioned hemostasis valve housing (12) to be opened and closed in the manner described is within the scope of coverage of this invention.

Preferably, the inner edges (90, 91, 92, 93) of each body section (26, 28) of the partitioned hemostasis valve housing (14) are formed with a structure which assists in the joining and sealing of the body sections (26, 28) together. For example, in one preferred embodiment, as shown in FIG. 3, both inner edges (90, 91) of one body section (26) of the partitioned hemostasis valve housing (12) contain a groove section (96, 97), while both opposing edges (92, 93) of the corresponding body section (28) contain a tongue section (94, 95), which fits within the groove sections (96, 97), and assist in securing the two body sections (26, 28) together. This tongue-in-groove system also assists in aligning the respective components of the body sections (26, 28), the respective hemostasis valve sections (38, 40) and the respective sides (114, 116) of the adaptor system (18).

Figure 10:
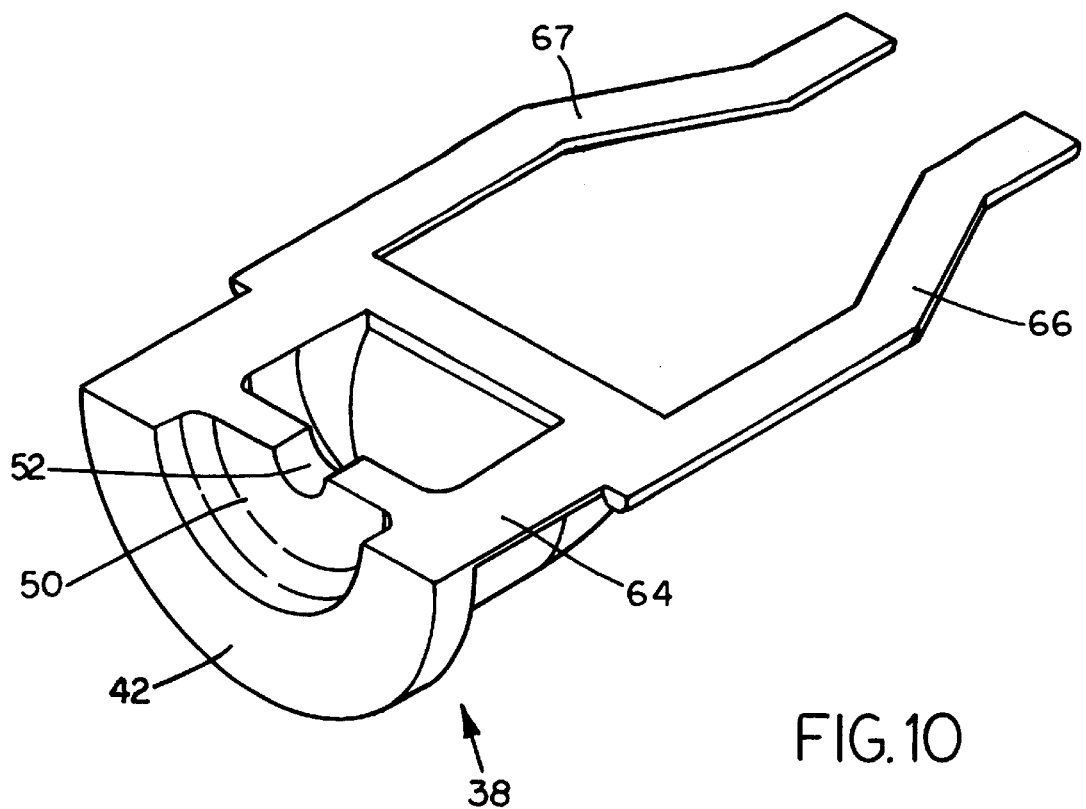
FIG. 10 is a perspective view of an alternative embodiment of the invention showing an extended seal secured to one of the partitioned hemostasis valve sections of the partitioned hemostasis valve.
Figure 11:
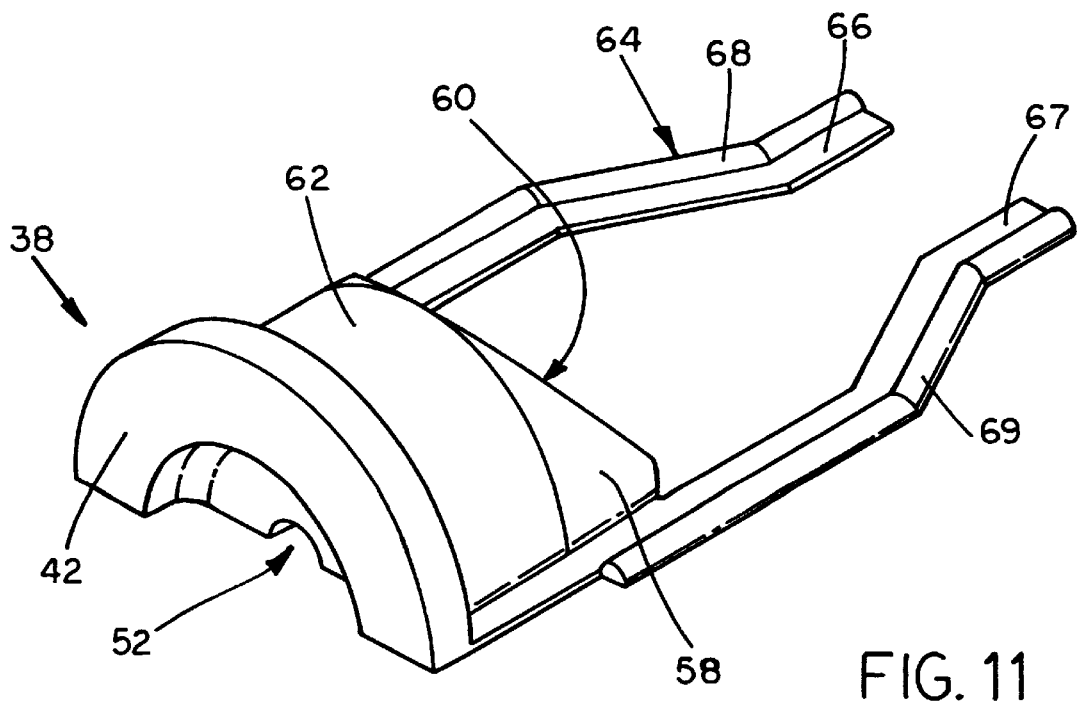
FIG. 11 is a perspective view of the alternative embodiment of the partitioned hemostasis valve section of FIG. 10 rotated 180 degrees.

In an alternative embodiment an extended seal (64) is secured to one of the hemostasis valve sections (38, 40) as shown in FIGS. 10 and 11. This extended seal (64) assists in sealing the hemostasis valve sections (38, 40) of the partitioned hemostasis valve (14) together. This extended seal (64) is generally a thin seal formed in the shape of the inner edge of the hemostasis valve section (38) and may be secured to the inner edge of the hemostasis valve section (38) by a conventional sealing method, such as gluing. However, in a preferred embodiment the extended seal (64) is formed as an integral element of the hemostasis valve section (38) during the forming of the hemostasis valve section (38). Preferably, the extended seal (64) also includes a pair of extended leg portions (66, 67) which extend downward from the hemostasis valve section (38). The extended leg portions rest against the inside surfaces (90, 91) of the respective body section (26). In one preferred embodiment, as shown in FIG. 11, the back side of the extended leg portions (66, 67) contains tongue portions (68, 69). These tongue portions (68, 69) fit within the grooves (96, 97) in the inner edges (90, 91) of the respective body section (26). The extended seal (64) is formed of the same type of material as is the partitioned hemostasis valve (14) and assists in sealing not only the respective hemostasis valve sections (38, 40), but also the respective body sections (26, 28).

To further assist in retaining the two body sections (26, 28) in a closed position, as shown in FIGS. 1 and 4, preferably a locking system (100) is secured to the partitioned hemostasis valve housing (12). In one preferred embodiment as shown in FIGS. 3 and 4, the locking system (100) includes an external snap section (102), secured to one body section (26) of the partitioned hemostasis valve housing (12), which cooperates with an indented section (104), which is secured to the other body section (28). The snap section (102) snaps into the indented section (104) when the two body sections (26, 28) are forced together to hold securely the components of the partitioned hemostasis valve housing (12) together in a closed position and reduce the likelihood of leakage of blood from the partitioned hemostasis valve system (10).

Secured to one of the body sections (28) of the partitioned hemostasis valve housing (12) in one embodiment is a side port (120) as shown in FIGS. 1, 2 and 3. This side port (120) provides access to the central chamber (13) of the partitioned hemostasis valve housing (12). When the side port (120) is used, an extension tube (122) and a fitting, such as a stopcock (124) may be attached to this side port (120) to permit introduction or withdrawal of fluids from the partitioned hemostasis valve housing (12).

In a preferred embodiment, as shown in FIGS. 3, 4 and 5, the partitioned hemostasis adaptor system (18) is secured to the opposite end of the partitioned hemostasis valve housing (14) from the cap sections (22, 24). This system (18) is designed to hold securely the splittable sheath (20), for example, as shown in FIGS. 1 and 2. In a preferred embodiment, this partitioned adaptor system (18) includes a pair of sides (114, 116). When the two sides (114, 116) are brought together, they create a structure which holds the T-shaped top of the splittable sheath (20), such as is disclosed in FIG. 3 of U.S. Pat. No. 5,098,392, which is incorporated herein by reference, to the partitioned hemostasis valve housing (12). In a preferred embodiment a split gasket (112, 113) as shown in FIG. 5 is secured to the partitioned adaptor system (18), with one half of the gasket (112) secured to one side (114) of the adaptor system (18) and the other half (113) secured on the opposite side (116) of the adaptor system (18). These gaskets (112, 113) are preferably formed from a heavy duty, rubber-like material, such as a silicone rubber of 10–40 durometer, which forms a tight seal around the T-fitting of the splittable sheath (20).

This splittable sheath (20), as shown in FIGS. 1 and 2 is preferably comprised of a generally elongated, substantially cylindrical tube (202) having a handle (204) fixed to its proximal end (206). It can be formed of any suitable plastic material, preferably a polyethylene or tetrafloroethylene plastic, wherein the plastic is compatible with body fluids, particularly blood. The tube (202) has a proximal end (206)

and distal end (208) and mechanically formed, longitudinally extending zones of reduced thickness (not shown) defined by internally scored, longitudinally shallow grooves or indentations running the length of the tube (202). The handle (204) preferably includes a pair of handle members (212) projecting perpendicularly outward from the cylindrically shaped tube (202). Upon pressure being placed against the top of the handle members (212), the tube (202) splits for removal from the patient.

In operation, the vessel of the patient is first pierced by a needle with a guide wire threaded through the lumen of the needle into the vessel. The needle is then removed leaving the guide wire in the vessel with a portion exposed. The dilator (300) and splittable sheath (20) are then advanced together over the guide wire into the vessel. The splittable sheath (20) is then advanced into the appropriate location within the body and the guide wire and dilator (300) are removed. The distal end of a medical device, such as a pacemaker lead, is then advanced through the splittable sheath (20), into the location within the patient for its utilization. The partitioned hemostasis valve system (10) is then secured onto the proximal end (206) of the splittable sheath (20) around its handle (204) over the device or lead. It may be attached at any time during the medical procedure, before or after the lead is placed in the sheath (20). The split gasket (112, 113) of the partitioned adaptor system (18) forms a tight fit around the handle (204) of the splittable sheath (20) to hold it securely in place and prevent blood leakage between the handle (204) of the splittable sheath (20) and the partitioned hemostasis valve system (10). Because the hemostasis valve sections (38, 40) are forced together, the partitioned hemostasis valve (14) acts like a conventional hemostasis valve, minimizing the amount of blood loss during the procedure.

Once the pacemaker lead has been placed in the appropriate location, the partitioned hemostasis valve system (10) can be opened by forcing together the pivotable wing sections (70, 71) which in turn open the body sections (26, 28) of the partitioned hemostasis valve housing (12) and the hemostasis valve sections (38, 40). By opening the partitioned hemostasis valve housing (12), the splittable sheath (20) is also released from the hemostasis valve system (10). Because the partitioned hemostasis valve sections (38, 40) are also separated during this procedure, the partitioned hemostasis valve system (10) can be removed from the operating theater. However, because the partitioned hemostasis valve (14) has not been torn apart, the partitioned hemostasis valve system (10) can be reattached to the splittable sheath (20), if necessary, consistent with appropriate medical procedure. The splittable sheath (20) may then be removed from the operating theater by splitting it apart by downward pressure on the handle members (212).

It will be apparent from the foregoing that while particular forms of the invention have been illustrated and described, various modifications may be made without departing from the spirit and scope of the invention.

I claim:

1. A partitioned hemostasis valve system comprising
   a partitioned hemostasis valve housing comprising a plurality of hemostasis valve housing body sections, which form a central chamber, and a hemostasis valve separation system;
   a partitioned hemostasis valve secured within the central chamber comprising a plurality of hemostasis valve sections; and
   a partitioned adaptor system secured to the partitioned hemostasis valve housing comprising a plurality of adaptor system sides, wherein said partitioned adaptor system is structured to hold a splittable sheath, wherein a partitioned gasket is secured to the partitioned adaptor system, and wherein the partitioned gasket forms a seal about the splittable sheath.

2. The partitioned hemostasis valve system of claim 1 wherein the partitioned hemostasis valve housing further comprises a partitioned cap comprising a plurality of cap sections, wherein one of the cap sections secures one of the partitioned hemostasis valve sections to one of the partitioned hemostasis valve body sections.

3. The partitioned hemostasis valve system of claim 1 further comprising a side port with extension tube secured to the partitioned hemostasis valve housing.

4. A partitioned hemostasis valve system comprising
   a partitioned hemostasis valve housing comprising a plurality of hemostasis valve housing body sections, which form a central chamber, and a hemostasis valve separation system;
   a partitioned hemostasis valve secured within the central chamber comprising a plurality of hemostasis valve sections, wherein one of the partitioned hemostasis valve sections is secured to one of the partitioned hemostasis valve body sections, wherein one of the partitioned hemostasis valve body sections further comprises a grooved section, and wherein a second partitioned hemostasis valve body section further comprises a tongue section, and wherein said tongue section fits within said grooved section; and
   a partitioned adaptor system secured to the partitioned hemostasis valve housing comprising a plurality of adaptor system sides, wherein said partitioned adaptor system is structured to hold a splittable sheath.

5. The partitioned hemostasis valve system of claim 4 wherein the partitioned hemostasis valve housing further comprises a partitioned cap comprising a plurality of cap sections, wherein one of the cap sections secures one of the partitioned hemostasis valve sections to one of the partitioned hemostasis valve body sections.

6. The partitioned hemostasis valve system of claim 4 further comprising a side port with extension tube secured to the partitioned hemostasis valve housing.

7. The partitioned hemostasis valve system of claim 4 further comprising an extended seal secured to one of the partitioned hemostasis valve sections.

8. The partitioned hemostasis valve system of claim 7 wherein the extended seal further comprises an extended leg portion secured to one of the partitioned hemostasis valve body sections.

9. The partitioned hemostasis valve system of claim 8 wherein the extended leg portion further comprises a tongue portion securable within a groove contained in one of the partitioned hemostasis valve body section.

10. A partitioned hemostasis valve system comprising
    a partitioned hemostasis valve housing comprising a plurality of hemostasis valve housing body sections, which form a central chamber, and a hemostasis valve separation system, wherein one of the partitioned hemostasis valve body sections further comprises a snap fitting and a second partitioned hemostasis valve body sections further comprises an indented section, wherein the snap fitting and the indented section interact to hold the partitioned hemostasis valve body sections together;
    a partitioned hemostasis valve secured within the central chamber comprising a plurality of hemostasis valve sections; and a partitioned adaptor system secured to the partitioned hemostasis valve housing comprising a plurality of adaptor system sides, wherein said partitioned adaptor system is structured to hold a splittable sheath.

11. The partitioned hemostasis valve system of claim 10 wherein the partitioned hemostasis valve housing further comprises a partitioned cap comprising a plurality of cap sections, wherein one of the cap sections secures one of the partitioned hemostasis valve sections to one of the partitioned hemostasis valve body sections.

12. The partitioned hemostasis valve system of claim 10 further comprising a side port with extension tube secured to the partitioned hemostasis valve housing.

13. A partitioned hemostasis valve system comprising a partitioned hemostasis valve housing comprising a plurality of hemostasis valve housing body sections, which form a central chamber, and a hemostasis valve separation system, wherein the hemostasis valve separation system comprises a plurality of wing sections, each of which is secured to the partitioned hemostasis valve housing, a pivot pin opening contained in the wing sections, a pivot pin and a spring;

a partitioned hemostasis valve secured within the central chamber comprising a plurality of hemostasis valve sections; and a partitioned adaptor system secured to the partitioned hemostasis valve housing comprising a plurality of adaptor system sides, wherein said partitioned adaptor system is structured to hold a splittable sheath.

14. The partitioned hemostasis valve system of claim 13 wherein the partitioned hemostasis valve housing further comprises a partitioned cap comprising a plurality of cap sections, wherein one of the cap sections secures one of the partitioned hemostasis valve sections to one of the partitioned hemostasis valve body sections.

15. The partitioned hemostasis valve system of claim 13 further comprising a side port with extension tube secured to the partitioned hemostasis valve housing.

16. The partitioned hemostasis valve system of claim 13 wherein the spring encourages the hemostasis valve body sections together.

17. The partitioned hemostasis valve system of claim 13 wherein pressure placed on an outside edge of the wing sections results in the partitioned hemostasis valve housing body sections moving apart.

18. A partitioned hemostasis valve system comprising a partitioned hemostasis valve housing comprising a plurality of hemostasis valve body sections, which form a central chamber, and a hemostasis valve separation system;

a partitioned hemostasis valve secured within the central chamber comprising a plurality of hemostasis valve sections;

a partitioned adaptor system secured to the partitioned hemostasis valve housing comprising a plurality of adaptor system sides, wherein said partitioned adaptor system is structured to hold a splittable sheath, wherein the splittable sheath is secured to the partitioned adaptor system; and a partitioned gasket secured to the partitioned adaptor system, wherein said partitioned gasket forms a seal about the splittable sheath.

19. The partitioned hemostasis valve system of claim 18 wherein the partitioned hemostasis valve housing further comprises a partitioned cap comprising a plurality of cap sections, wherein one of the cap sections secures one of the partitioned hemostasis valve sections to one of the partitioned hemostasis valve body sections.

20. The partitioned hemostasis valve system of claim 18 further comprising a side port with extension tube secured to the partitioned hemostasis valve housing.

21. The partitioned hemostasis valve system of claim 18 wherein one of the partitioned hemostasis valve sections is secured to one of the partitioned hemostasis valve body sections.

22. The partitioned hemostasis valve system of claim 21 further comprising an extended seal secured to one of the partitioned hemostasis valve sections.

23. The partitioned hemostasis valve system of claim 22 wherein the extended seal further comprises an extended leg portion secured to one of the partitioned hemostasis valve body sections.

24. The partitioned hemostasis valve system of claim 23 wherein the extended leg portion further comprises a tongue portion secured within a groove contained in the partitioned hemostasis valve body section.

25. The partitioned hemostasis valve system of claim 18 wherein one of the partitioned hemostasis valve body sections further comprises a grooved section, and wherein a second partitioned hemostasis valve body section further comprises a tongue section, and wherein said tongue section fits within said grooved section.

26. The partitioned hemostasis valve system of claim 18 wherein one of the partitioned hemostasis valve body sections further comprises a snap fitting and a second partitioned hemostasis valve body sections further comprises an indented section, wherein the snap fitting and the indented section interact to hold the partitioned hemostasis valve body sections together.

27. The partitioned hemostasis valve system of claim 18 wherein the hemostasis valve separation system comprises a plurality of wing sections, each of which is secured to the partitioned hemostasis valve housing, a pivot pin opening contained in the wing sections, a pivot pin and a spring.

28. The partitioned hemostasis valve system of claim 27 wherein the spring encourages the hemostasis valve body sections together.

29. The partitioned hemostasis valve system of claim 27 wherein pressure placed on an outside edge of the wing section results in the partitioned hemostasis valve housing body sections moving apart.

* * * * *